(12) United States Patent
Hadváry et al.

(10) Patent No.: US 10,420,488 B2
(45) Date of Patent: Sep. 24, 2019

(54) DIAGNOSTIC DEVICE

(75) Inventors: Paul Hadváry, Biel-Benken (CH); Hansjörg Tschirky, Sissach (CH)

(73) Assignee: PHARMASENS AG, Biel-Benken (CH)

( * ) Notice: Subject to any disclaimer, the term of this patent is extended or adjusted under 35 U.S.C. 154(b) by 799 days.

(21) Appl. No.: 13/877,480

(22) PCT Filed: Sep. 16, 2011

(86) PCT No.: PCT/EP2011/066074
§ 371 (c)(1),
(2), (4) Date: May 30, 2013

(87) PCT Pub. No.: WO2012/045561
PCT Pub. Date: Apr. 12, 2012

(65) Prior Publication Data
US 2013/0253289 A1 Sep. 26, 2013

(30) Foreign Application Priority Data

Oct. 4, 2010 (EP) ...................................... 10186398

(51) Int. Cl.
*A61B 5/145* (2006.01)
*A61B 5/15* (2006.01)
(Continued)

(52) U.S. Cl.
CPC ...... *A61B 5/14528* (2013.01); *A61B 5/14503* (2013.01); *A61B 5/14514* (2013.01);
(Continued)

(58) Field of Classification Search
CPC ............... A61M 5/172; A61B 5/14528; A61B 5/15128; A61B 5/15016; A61B 5/1405;
(Continued)

(56) References Cited

U.S. PATENT DOCUMENTS

| 5,931,814 A * | 8/1999 | Alex ................. A61M 5/14248 |
| | | 604/131 |
| 6,695,860 B1 * | 2/2004 | Ward ....................... A61B 5/00 |
| | | 600/505 |

(Continued)

FOREIGN PATENT DOCUMENTS

| WO | WO 03/055540 A1 | 7/2003 |
| WO | WO 2005/063115 A1 | 7/2005 |

(Continued)

*Primary Examiner* — Meredith Weare
(74) *Attorney, Agent, or Firm* — XSensus LLP

(57) ABSTRACT

An improved diagnostic analyte monitoring device has partially retractable hollow guide needles for the intradermal placement of diagnostic elements fixedly connected to measuring means within this device obviating the need to remove the guide needle and to connect the diagnostic elements to measuring means after placement into the skin. A flexible surface adhering to the skin serves for the subcutaneous implantation of the diagnostic elements within the guide needles and partial retraction of the guide needles exposes the active surface to body fluid, actuated by means designed for easy handling and safe operation. Concentration-time profiles of endogenous and exogenous analytes measured with the device are used to improve drug treatment modalities on an individualized basis.

19 Claims, 5 Drawing Sheets

(51) Int. Cl.
*A61B 5/151* (2006.01)
*A61B 5/157* (2006.01)
*A61B 5/00* (2006.01)
*A61M 5/172* (2006.01)
*A61M 5/142* (2006.01)

(52) U.S. Cl.
CPC .......... *A61B 5/157* (2013.01); *A61B 5/15016* (2013.01); *A61B 5/150022* (2013.01); *A61B 5/15111* (2013.01); *A61B 5/15117* (2013.01); *A61B 5/15128* (2013.01); *A61B 5/15144* (2013.01); *A61B 5/150389* (2013.01); *A61B 5/150519* (2013.01); *A61B 5/150664* (2013.01); *A61B 5/150709* (2013.01); *A61B 5/6848* (2013.01); *A61B 5/145* (2013.01); *A61B 5/14532* (2013.01); *A61B 5/150229* (2013.01); *A61M 5/1723* (2013.01); *A61M 2005/14252* (2013.01)

(58) Field of Classification Search
CPC .......... A61B 5/150519; A61B 5/15111; A61B 5/15144; A61B 5/157; A61B 5/14514; A61B 5/150664; A61B 5/150389; A61B 5/6848; A61B 5/150709; A61B 5/15117; A61B 5/150022; A61B 5/145
See application file for complete search history.

(56) References Cited

U.S. PATENT DOCUMENTS

| | | | | |
|---|---|---|---|---|
| 7,066,907 | B2* | 6/2006 | Crossman | A61M 5/2033 604/110 |
| 9,101,304 | B2* | 8/2015 | Lindgren | A61B 5/14528 |
| 2003/0093036 | A1* | 5/2003 | Crossman | A61M 5/2033 604/197 |
| 2005/0119588 | A1 | 6/2005 | Model et al. | |
| 2006/0020312 | A1 | 1/2006 | Eggers et al. | |
| 2007/0191701 | A1* | 8/2007 | Feldman | A61B 5/14514 600/347 |
| 2007/0287952 | A1* | 12/2007 | Shah | A61B 5/145 604/27 |
| 2008/0027296 | A1 | 1/2008 | Hadvary et al. | |
| 2008/0146904 | A1* | 6/2008 | Hunn | A61B 5/14532 600/365 |
| 2010/0113907 | A1* | 5/2010 | Schwind | A61B 5/14532 600/345 |
| 2011/0190597 | A1 | 8/2011 | Marnay et al. | |
| 2011/0213230 | A1* | 9/2011 | Lindgren | A61B 5/14528 600/365 |
| 2011/0313357 | A1* | 12/2011 | Skutnik | A61M 5/14248 604/151 |
| 2015/0141776 | A1* | 5/2015 | Hadvary | A61M 5/158 600/309 |

FOREIGN PATENT DOCUMENTS

| | | | | |
|---|---|---|---|---|
| WO | WO-2008/135453 | A1 * | 11/2008 | .............. A61B 5/00 |
| WO | WO 2009/109215 | A1 | 9/2009 | |
| WO | WO-2010/002350 | A1 * | 1/2010 | .............. A61M 1/16 |

* cited by examiner

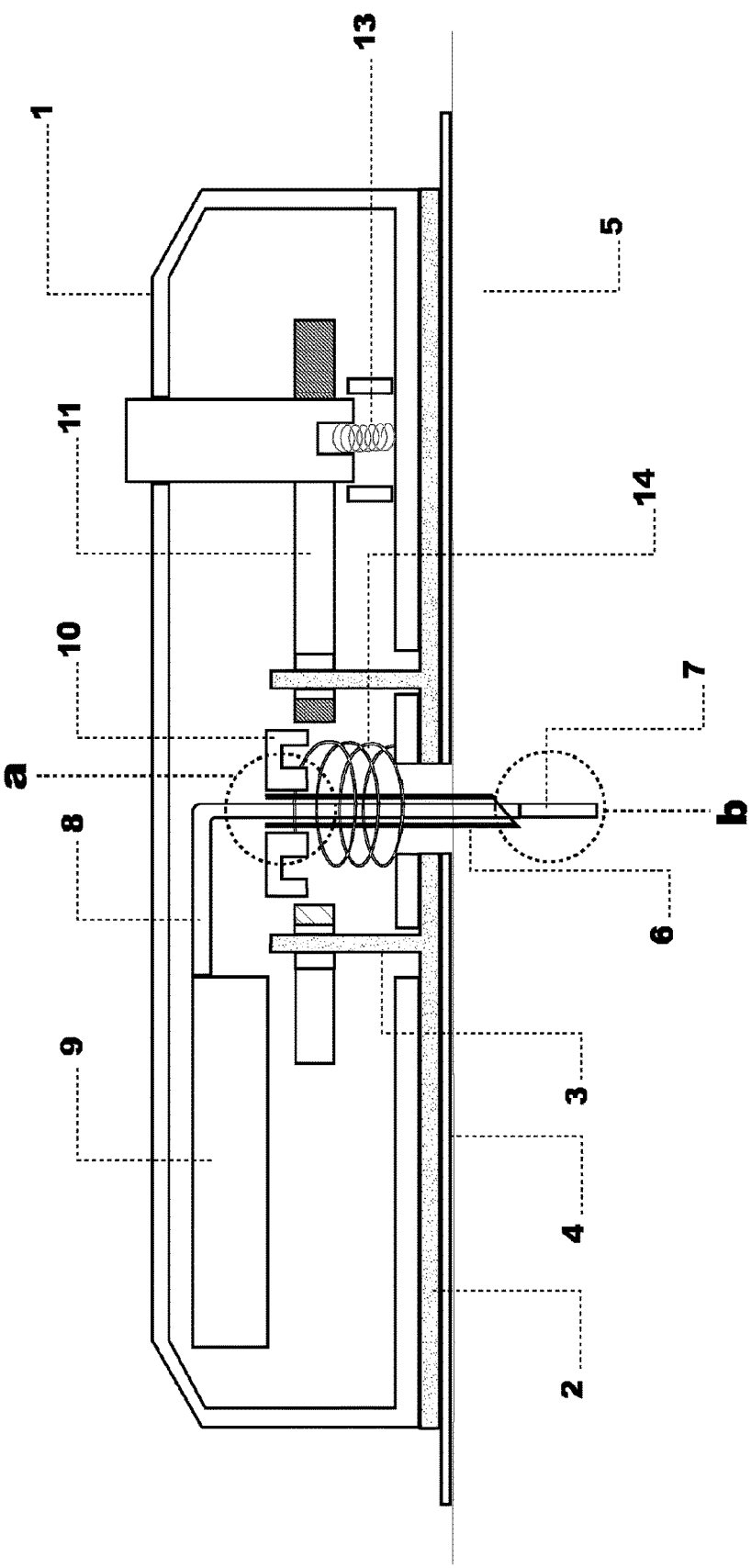

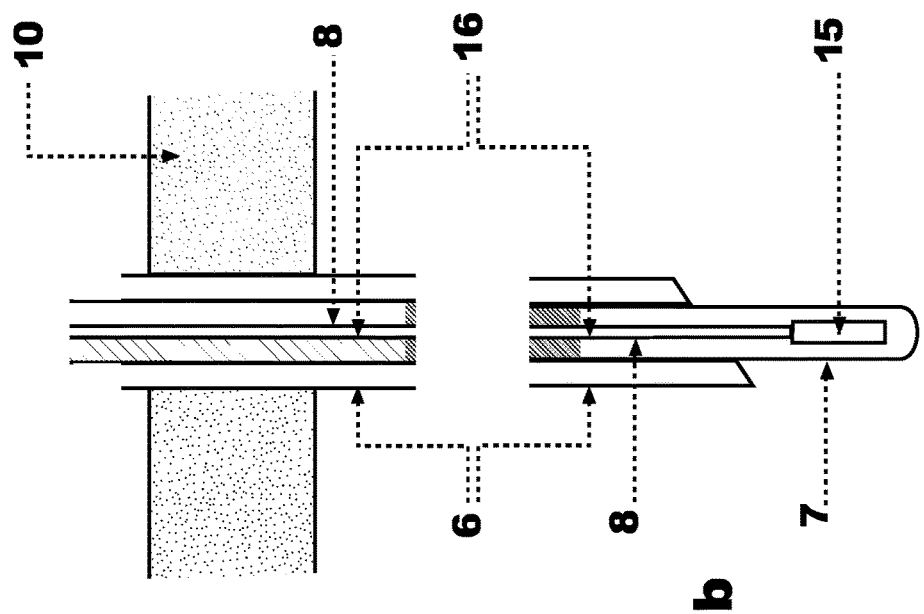

Fig. 3
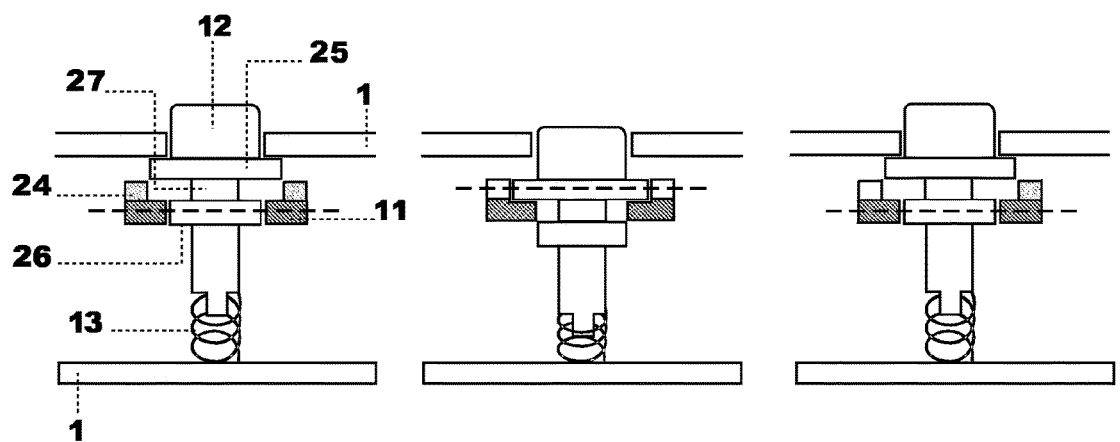
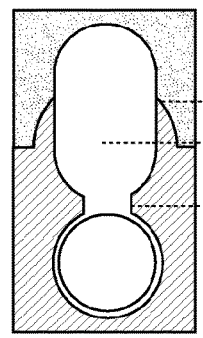
Fig. 3a
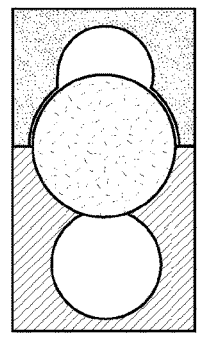
Fig. 3b
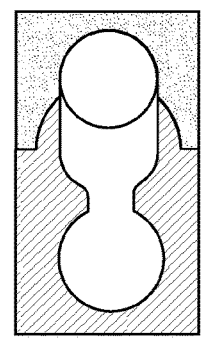
Fig. 3c

DIAGNOSTIC DEVICE

The invention relates to a method and a device for exposing an active surface of a diagnostic element to body fluid for the measurement of the concentration of an analyte comprising a hollow guide needle penetrating through the skin of a patient and housing the active surface and connection lines to measuring means of the diagnostic element.

The monitoring of the level of endogenous analytes such as glucose, lactate, creatinine or oxygen, in certain individuals, is vitally important for their health. Certain substances such as glucose can also be administered for diagnostic stress-tests. In addition, monitoring of the level of xenobiotics such as insulin, and certain drugs and their metabolites is important for diagnosis of e.g. kidney and liver function and can be vitally important for the choice and correct dosing in drug treatment. For a chosen drug, monitoring of its pharmacokinetics under treatment conditions in a given patient can allow individualized optimization of the treatment schedule and help to avoid potentially serious drug-drug interactions. For such applications a reliable device which allows monitoring of analyte concentration in body fluids such as e.g. subcutaneous interstitial fluid for several hours to a few days is necessary. To achieve acceptance from patients and for use in an out-patient setting, convenience and minimal invasiveness are extremely important features.

A convenient alternative to frequent blood sampling is to measure the concentration of the analyte in dermal interstitial fluid since the concentration of certain analytes such as e.g. glucose is highly correlated between these two fluid compartments (Bantle, et al., J Lab Clin Med 1997; 130: 436-441, Boyne et al., Diabetes 2003; 52: 2790-2794). Sensors for e.g. glucose monitoring in interstitial fluid are known in the art, for example U.S. Pat. No. 6,579,690, published Jun. 17, 2003 by Bonnecaze et al., US Patent Application 20070249922, published Oct. 25, 2007 by Peyser et al. (see also review by Heller and Feldman, Chemical Reviews 2008, 108: 2482-2505). In patent applications various embodiments of such sensor devices are described. One important feature of these devices as well as of devices prior in the art is that the sensor is first implanted into the body and in a second step, on the patient, has to be connected to a control unit. Such a procedure, especially with miniaturized components, needs a high level of skill and the use of mounting tools is foreseen, but relatively complicated for handling in several steps. These drawbacks severely limit the acceptance and can easily lead to incorrect functioning. Fully implantable sensors including wireless transmitters avoid the problems of mounting together the several components following implantation of the sensor. On the other hand, their size necessitates a surgical procedure for implantation with the associated inconveniences for the patient and needs qualified health care professionals for the implantation. The damage inflicted on the subcutaneous tissue upon implantation of the sensor is dependent on the size and shape of the sensor or implantation guide and results in inflammatory tissue reactions which can alter the performance of the sensor and even lead to changes in the availability of analytes surrounding the sensor. Therefore, for reliable measurements, minimal invasiveness is very important. This can only be achieved by miniaturization of the implanted parts of the sensor and optimization of the sensor shape and insertion means to avoid tissue damage upon insertion as much as possible.

Most sensors and insertion mechanisms of prior art are far from optimal in this respect.

To circumvent the inherent handling problems with implantable sensors, several approaches were taken to e.g. withdraw subcutaneous fluid by making holes into the skin by lancing or with a laser beam, or to withdraw fluid with an electric current. Since the volume which can be withdrawn by these means is very small, usually below 1 µl, the determination of analyte concentrations is technically difficult and not reliable and many factors, e.g. sweating can lead to changes of the composition and to massively wrong determinations.

In a patent application by Hadvary and Tschirky (EP1706019 (A1), published Oct. 17, 2006) a solution to overcome some of the above mentioned problems was described by incorporating tailored functional elements such as sensor, implantation means and measuring means into one single device unit which is attached to the skin of the patient. The described solution is however applicable only to rigid sensors, which can be used directly for piercing the skin for implantation. Most established technologies resulting in rigid miniaturized sensors are based on core material that is brittle at these dimensions, e.g. silicon, and therefore is not suited for subcutaneous sensors. Other established technologies for sensors are based e.g. on flexible plastic substrates which can be inserted into the skin only with the help of a rigid guide, which is then removed following the implantation of the flexible sensor. In order to allow removal of the rigid guide usually a U shaped cannula-type guide is being used, as e.g. described in a patent application by Huss, Stafford et. al. (CA2636034 (A1), published Oct. 25, 2007) which limits the degree of possible miniaturization since, besides manufacturing difficulties, a very thin wall of the lateral side of the U inevitably results in a cutting edge and therefore in substantial tissue damage.

The aim of the present invention is to overcome the current problems with the insertion of miniaturized subcutaneous sensors and other diagnostic elements needing a guide for implantation.

According to the invention this is achieved in that after its insertion the hollow guide needle is only partially retracted, thereby exposing the active surface at the tip of the diagnostic element to body fluid without interfering with the connection lines of the diagnostic element. A device for performing this method has a hollow guide needle accommodating loosely in its lumen the active surface and the connection lines of the diagnostic element and means for partially retracting the guide needle following the implantation.

During partial retraction the guide needle is sliding over the connection lines of the diagnostic element but the connecting elements to measuring means at the other end of the connection lines remain outside of the needle and therefore there is no need for a U shaped guide with a slit opening allowing the entire retraction and removal of the guide.

Hollow needles with a smooth, cylindrical surface are minimizing tissue damage and sensation upon insertion into the skin. In contrast, miniaturized U shaped cannula-type guides, because of the thin walls, inevitably result in cutting edges like a scalpel which lead to substantial tissue damage and bleeding. The problem with the removal of a hollow guide needle after implantation is overcome by partial retraction of the guide needle allowing the exposure of the active surface of the diagnostic element to tissue fluid. A solution with pre-fabricated connection of fixedly positioned conducting elements with other functional elements within the device is also disclosed leading to user-friendly and safe operation even with miniaturized structures. Further, tailored functional elements such as means for a controlled insertion of the guide needle with the diagnostic element first, and partial retraction of the guide needle as a second step, in sequence, as well as means for functional packaging which contribute to safe handling are disclosed. In a preferred embodiment the diagnostic elements have an active surface and conducting part which consists of a flexible plastic surface, less than 0.3 mm in width, with a prefabricated connection between conducting part and the other functional elements within the device, and guide needles, insertion mechanism, control and measuring means are all incorporated into one single device unit which is attached to the skin of the patient. Further, preferentially an insertion mechanism described by Hadvary and Tschirky (EP1706019 (A1), published Oct. 17, 2006) is used for insertion of the guide needle into the skin circumventing the need to move the diagnostic elements relative to all the other elements included in the device. This allows a simpler construction and higher reliability with safe performance as compared to moving elements or connections which have to be established by the user. Following placing the device on the skin using the disclosed functional packaging, which secures safe adhesion to the skin, implantation of the sensor and start of the measurements can be accomplished with one single and easy manipulation step, such as pressing a release button. Such a construction allows also for an unprecedented miniaturization and optimization of the design for the implanted part of the diagnostic elements and of the guide needle, thus becoming minimally invasive and therewith painless and of high reliability. In addition, the partially retractable guide needle of the subject invention can accommodate many different types of miniaturized diagnostic elements in an optimal way.

The terms used in this specification are to be understood according to the following definitions:

"Adhesive layer" for temporary wearing on the skin is made of materials with strong adhesive properties, stretchability and minimal allergenicity. This adhesive layer is fixed on the flexible base of the device in such a way that it does not interfere with its flexibility. Preferentially the surface of the adhesive layer which is fixed to the skin is significantly larger than its surface which is fixed to the flexible base of the device. This can be accomplished e.g. by an adhesive layer extending beyond the surface of the base of the device or, preferentially by using a shape for the adhesive surface to the skin similar to or only slightly larger than the surface of the flexible surface of the device but fixing it to the latter in such a way that an outer annular zone is not fixed to the base of the device. Such a design is described in EP0825882 for a medical device with a rigid base.

"Analyte" means any endogenous or exogenous substance the concentration of which can be used to diagnose the health, organ function, metabolic status, or drug metabolizing capacity of an individual. Examples of endogenous substances are glucose, lactate, oxygen, creatinine, etc. Examples of exogenous substances are drugs, metabolites of such drugs, diagnostic substances (e.g. inulin) etc.

"Body fluid" is interstitial fluid or blood.

"Component with a flexible surface" is made up of a casing which has preferentially a circular or oval footprint and which has a flexible base. This base plate is constructed in such a way that it can be deformed to a convex shape with a protruding part e.g. like a cone or a gable (position 1). An additional feature of this base is that it can shoot from the convex shape into a flat shape (position 2) with sufficient velocity and force that this movement can provide the driving energy for implantation of the sensors. Such a flexible surface can be achieved by appropriate segmentation of the surface with hinge regions acting as springs and/or by using elastic materials with the necessary reversible stretching characteristics which moves e.g. from a pre-stressed shape to adopt a flat, relaxed shape.

Means to position the flexible surface relative to the guide needles in two defined positions consists of elements which can bring about the deformation of the flexible surface to a convex, pre-stressed shape and allow a rapid release from this position to adopt a flat, relaxed shape in a coordinated way for the entire surface. This can be accomplished preferentially by several pin-shaped elements protruding from the flexible surface and pushing onto a sliding bolt mechanism, but other constructions using screws, ramps, levers etc. are also possible.

Such a component with a flexible surface can be manufactured by injection molding of suitable plastics but also by using other materials like steel, composite or ceramic materials, etc. The base of this element has an opening in form of a hole or slit, preferentially in the center, as opening for the guide needles. The guide needles are positioned axially to this base in such a way that in position 1 they are entirely covered up, whereas in position 2 they protrude the base.

"Control and measuring means" contains all necessary electronics and software elements for all necessary functions of the device like, but not limited to, initiating, controlling and surveying the correct functioning of the device, feeding and controlling the diagnostic elements and transforming sensor signals into analyte measurements, storing, displaying and transmitting analyte measurements online or batchwise, interacting with external control devices, preferentially wirelessly, and giving warning signals if the device is not functioning properly or if analyte measurements are not within a predefined range.

"Diagnostic element" is the functional element for the determination of analyte concentrations and means, but is not restricted to, any sensor, body fluid removal or microdialysis system.

The tip of diagnostic element comprising the active surface is in direct contact with the body fluid and exposes e.g. a sensor, an opening or a semi-permeable/dialysis membrane allowing the passage of the analyte from the body fluid to a fluid passing through the diagnostic element by a technique known as micro-dialysis. The active surface is part of an analytic or sample collecting system and is connected to the other system elements within the non-implanted part of the diagnostic element through a conducting part of the diagnostic element.

A sensor can contain one or more electrochemical, ion-selective, sonar, or surface plasmon resonance probes with electric or light conducting elements and can consist of functionally similar or different elements which are selective for one or several analytes The active surface of a sensor contains e.g. a probe at its surface which provides some signal (e.g. electrochemical, optic, thermometric, piezoelectric or magnetic) according to the concentration of the analyte. The surface of the sensor can be smooth or modeled in such a way that the sensor is mechanically protected. In addition, the surface can be increased by an appropriate geometry to increase the signal generated by the sensor. A variety of methods for the composition and structuring of suitable sensors has been described in the literature. These include also methods which prevent the leakage of components of the sensor while implanted into the skin and at the same time allow the diffusion of the analytes of interest e.g. by the use of suitable biocompatible polymers or by coating with semi-permeable membranes.

In the case of electrochemical sensors the sensors are constructed as electrodes selective for the chosen analyte e.g. glucose. In the case of optical sensors the active surface can be constructed as optical fibers and can contain also elements for the selective optical detection of analytes in form of suitable coating and sensors and/or measurement chambers. In the case of thermometric, piezoelectric or magnetic sensors, the active surface is constructed in such a way that it can transduce the respective signal in an optimal way.

An additional advantage of the present invention is that several sensors can be exactly positioned relative to each other, and an array can be constructed in such a way that they form parts of one measuring system such as working electrode and "counter electrode", or light source and light collector.

In case of a micro-dialysis system the active surface is a dialysis membrane forming the interface between the body fluid and a dialysis fluid which is passed at the other side of the membrane. In a preferred embodiment a micro-dialysis probe consists of an outer and an inner tube, covered at the implantable tip by a dialysis membrane. The inner tube is connected to a pump which delivers the dialysis fluid and the outer tube is connected to an analysis or collection element.

"Functional package" is designed to hold the rigid part of the device by a releasable coupling mechanism and has a removable cap to protect the active surface s of the sensors or diagnostic element during storage in a defined environment, such as humidity and allows maintaining sterility. The functional package has also a rim element allowing, after removal of the cap, the correct attachment of the rim of the adhesive layer by pressing against the skin. Further, the functional package protects the release/start mechanism of the device against premature, unintended operation and the release/start mechanism can be actuated only following attachment of the device to the skin and removal of the functional package.

"Guide needle" is a hollow needle with thin wall and an outer diameter below 1 mm which accommodates loosely in its lumen the active surface and part of the conductive part of the diagnostic elements, and has a tip and configured and being rigid enough to allow easy penetration of the skin. Insertion into the skin can be achieved in a minimally invasive and painless way if the diameter of this guide needle is very small, preferentially below 0.3 mm. The guide needle is preferentially equal or shorter than the conducting part of the diagnostic element. Upon insertion of the guide needle into the skin, containing the active surface and part of the conductive part of the diagnostic elements, the guide needle is only partially retracted, thereby exposing the tip with the active surface of the diagnostic element to the body fluid while the conducting part of the diagnostic element remains within the guide needle.

"A sliding bolt mechanism" adapts upon a circular or linear movement consecutively several fixed positions and consists of elements which display a closed or open state, for example a solid surface or a hole. The movement of the slide mechanism is driven for example by a spring and actuated by a release element, for example through pressing or releasing a button or handle, or through a minimal turning movement. Movement of the sliding bolt mechanism from the storage position (position 1) to the next position (position 2) upon an easy manipulation, e.g. by pressing a button actuating a rapid release of a flexible surface from a pre-stressed shape to adopt a flat, relaxed shape allows to actuate the movement of the sliding bolt mechanism to the next position (position 3) e.g. upon releasing the button, which actuates the partial retraction of the guide needle.

In the following a preferred embodiment of the invention is described with reference to the accompanying drawings, in which:

FIG. 2 shows a sectional view of the device in its operational mode

FIG. 2a,b show enlargements indicated in FIG. 2

Figure 3:
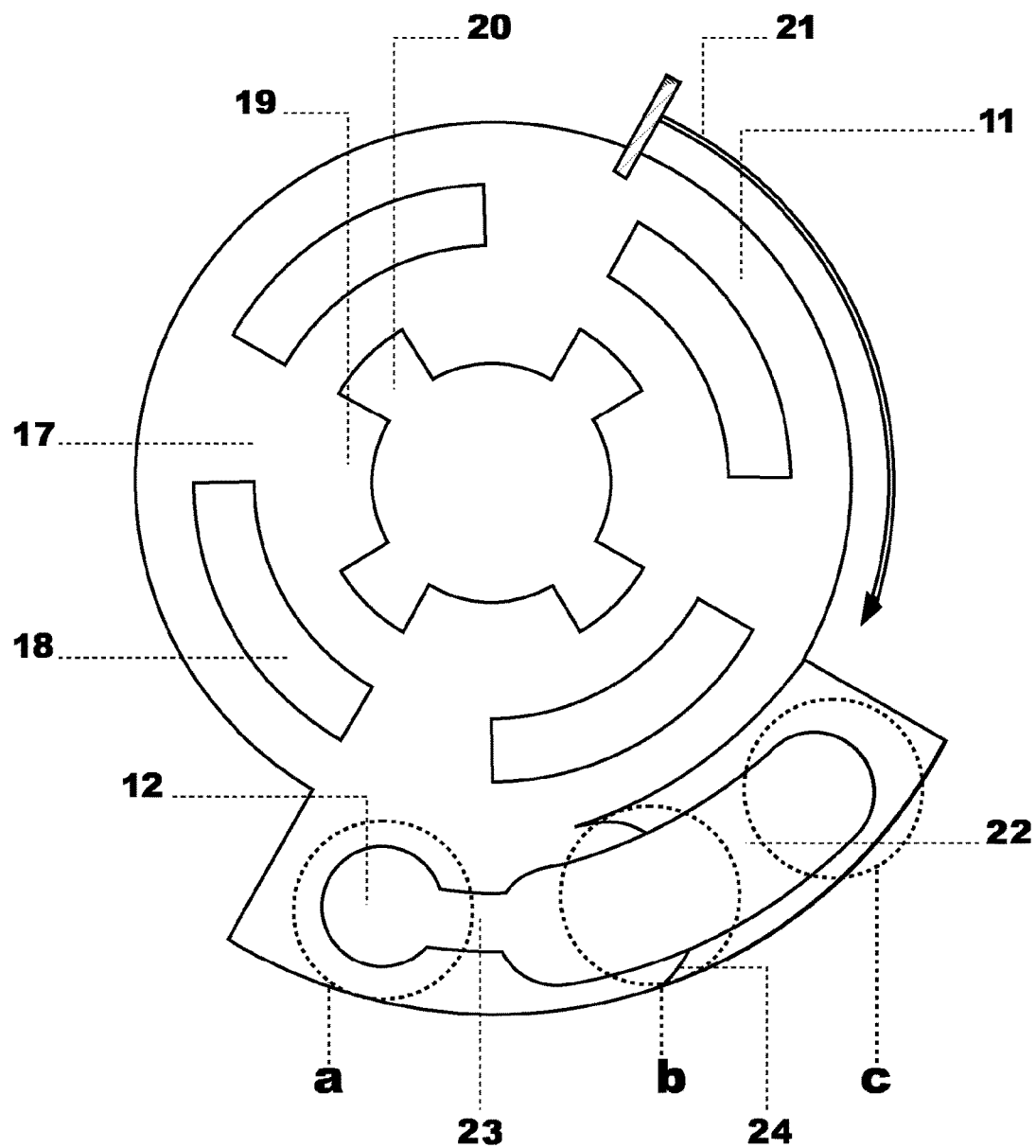

FIG. 3 is a diagrammatic representation of the sliding bolt mechanism actuating insertion of the guide needle into the skin and partial retraction of the guide needle in a consecutive way FIG. 3a-c show enlargements of areas indicated in FIG. 3, with sectional views above on top and a top views below This embodiment is a diagnostic device which can be worn and operated by the patient. The main aim of the present invention is a solution for the use of miniaturized diagnostic elements having a support which is not suited for direct insertion into the skin, e.g. flexprints or dialysis membranes and avoiding slit guide needles, which cannot be miniaturized below a certain limit. One aim of the present invention is to insert the diagnostic elements into the skin of a patient substantially without pain, thus avoiding the natural reluctance of the patient to invasive procedures and to reduce the reactions of the body to injury to a minimum. Another aim is to maintain an exact positioning of the active surface of the diagnostic elements relative to the device, to the skin and to each other leading to measurements with improved reliability. Further, immovable connections between the active surface of the diagnostic elements and the measuring equipment, which becomes possible according to the present invention, greatly improves the reliability of the diagnostic elements and makes the constructions much simpler. In addition, the necessary handling by the patient is reduced to a minimum of easy manipulations, like the pressing of a knob, which do not require nimble fingers for implanting the diagnostic elements and/or making the connections to the control and measuring instruments.

In contrast to known sensor devices, in the present inventive device the miniaturized active surface and the conducting part of the diagnostic elements are implanted into the skin within a needle with a smooth wall without a slit with sharp edges at the necessary level of miniaturization. Slit guide needles are generally used because they can be removed leaving the active surface implanted. According to the invention needles without a slit can be used if they are only partially retracted leaving the active surface exposed to body fluid. The guide needle housing the active surface and part of the conducting part of the diagnostic element is inserted into the skin by relaxing a pre-stressed flexible surface which is attached to the skin by means of an adhesive layer. After insertion into the skin the guide needle is partially retracted, exposing the active surface to the subcutaneous fluid.

Figure 1:
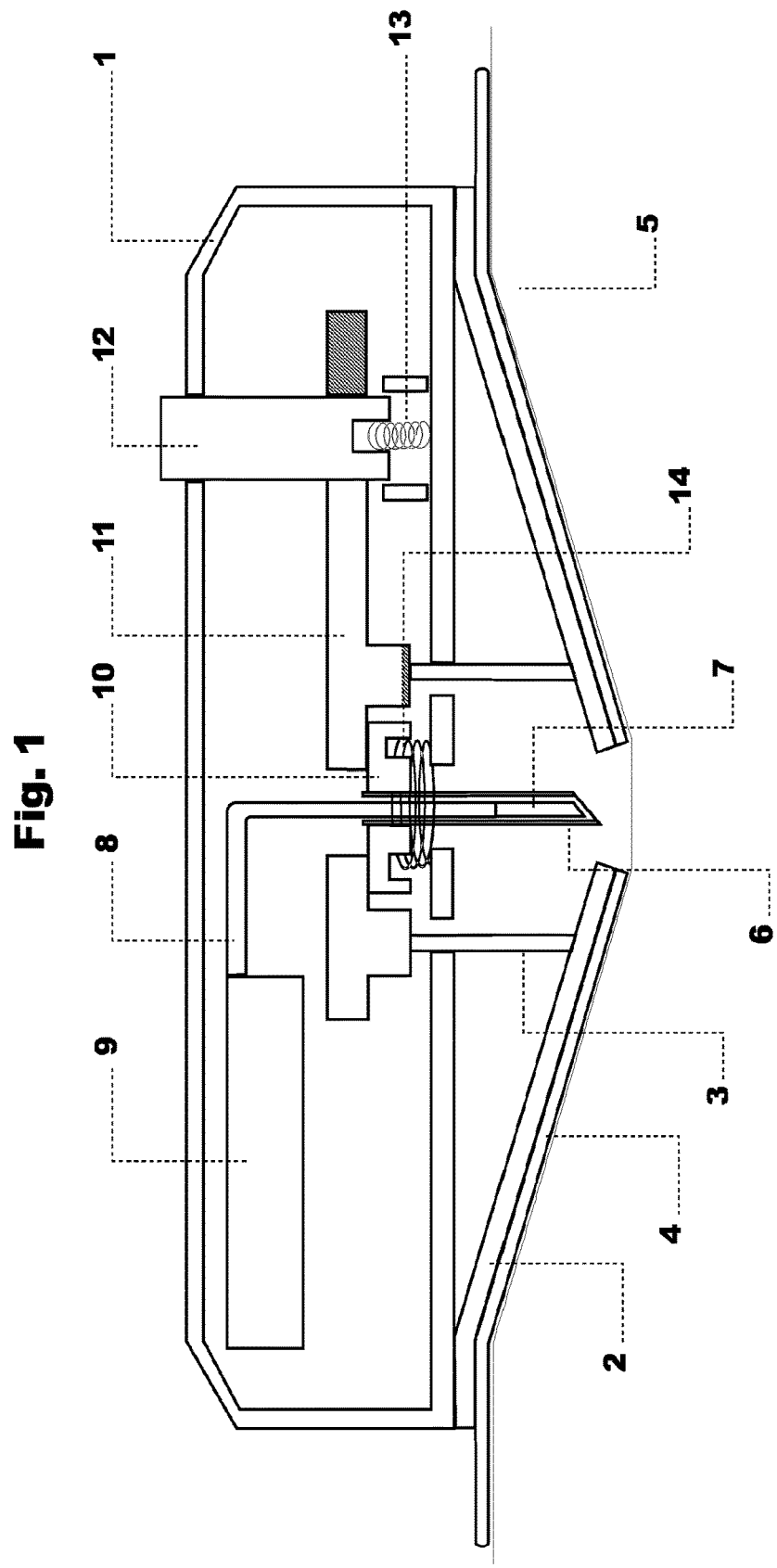
FIG. 1 shows a sectional view of the device in ready-to-use mode

In the ready-to-use state shown in FIG. 1, this flexible surface projects beyond the tips of the guide needles. In this position it holds the skin away from the tips when the device is placed on a suitable body area, preferably the abdomen, the thigh, the upper or the forearm, and by gentle pressing is attached by means of the adhesive layer. To insert the guide needles into the skin, the base plate is released from its pre-stressed position, preferentially by pressing an actuation knob. This activates a mechanism releasing the relaxation of the flexible surface into a flat shape. The skin attached to this flexible surface is moved relative to the guide needles and is penetrated by the tips. It has been found that a construction according to the present invention, with the flexible surface pre-stressed to form a cone by radial segmentation or in form of a gable, with a stretchable adhesive layer, can move the skin with enough impulse that miniaturized guide needles of even below 0.25 mm diameter can precisely be inserted into the skin basically without sensation and with minimal damage to the skin tissue. A construction which allows to operate the implantation process by pressing on a release mechanism like a knob vertically to the skin surface results in even better performance since adherence to the skin and the exact geometric positioning of the implanted parts of the sensors is greatly improved as compared e.g. to a rotary movement. Following insertion of the guide needle into the skin, partial retraction is actuated preferentially automatically and strictly consecutively, e.g. by a sliding bolt mechanism as shown in FIG. 3. After partial retraction of the guide needle the active surface of the diagnostic element becomes exposed to subcutaneous fluid, as depicted in FIG. 2 showing the device in operation mode. A great advantage of the construction according to the present invention compared to similar known devices is that no slit guide needles have to be used and all connections to the implanted parts of the diagnostic elements are rigid and no new connections have to be established after insertion—with known devices, such connections have to be established after the implantation of the sensors and slit guide needles cannot be sufficiently miniaturized without resulting in cutting edges.

As shown in FIG. 1 the diagnostic device has a casing having a cylindrical side-wall 1, a disk-like flexible base plate 2 in the pre-stressed position enforced by pins 3 of the flexible base plate, which is by means of an adhesive layer 4 attached to the skin 5. A guide needle 6 houses the active surface 7 and the adjacent portion of the connection lines or conductive part 8 of the diagnostic element which forms a rigid connection to control and measuring means 9. The guide needle 6 is fixed in a holder 10 at its end opposite to the tip and kept in the lowered position by a sliding bolt plate 11, which withholds also the pins 3 of the flexible base plate. An actuation knob 12 actuates the implantation and consecutive partial retraction of the guide needle, described in more detail with reference to FIG. 3, followed by starting the measuring process. In the ready-to-use state the actuation knob and the holder of the guide needle are pressed upwards against a stop by springs 13 and 14, respectively.

The base plate is preferentially annular or oval and has a radial segmentation, preferably into 5 to 8 segments with a spacing between them and a central concentric opening, forming a cone upon central bending or alternatively it consists of two segments with a diagonal slit, forming a gable upon bending. The segments are attached to the circumference of the casing by springy hinge regions and are in addition preferentially made of a flexible material. On its underside, the flexible base plate has an annular or oval adhesive layer for securing the device to the patient's skin with a concentric central opening or a diagonal slit, respectively similar to the base plate. This adhesive layer is composed of three parts, a glue for fixing to the flexible base plate, a textile providing the necessary flexibility and a glue for fixing onto the skin. Suitable materials with low allergenic potential are commercially available. The adhesive layer is protected during storage with a suitable sheet. In this example, the adhesive layer has a larger circumference than the device but it could have also the same circumference if the attachment to the base plate leaves an outer zone where it is not connected to the housing.

FIG. 2 shows the diagnostic device in the operational mode. The flexible base plate 2 is depicted in the relaxed, i.e. flat position. The pins 3 enforcing the pre-stressed position of the flexible base plate in the ready-to-use mode are now free in slits of the sliding bolt plate 11 and the holder of the guide needle 10 has passed through a hole of the sliding bolt plate by a slot and key construction and is hold in place by a stop (not shown). The guide needles and the active surfaces of the diagnostic elements protrude through the opening or slit of the base plate and of the adhesive layer and are inserted into the skin. A very important feature of the subject invention is that the connections between the active surfaces of the diagnostic elements implanted into the skin and the other parts of the device are stationary and therefore no connections have to be made manually after the implantation process. In addition, the present invention obviates the removal of the guide needle. As compared to similar devices of prior art this is a big advantage for reliability, easy handling and user acceptance.

The enlarged sectional view of FIG. 2a shows the holder of the guide needle 10 which fixes and retracts the guide needle 6 in a geometrically well defined movement, sliding over the conducting part of the diagnostic element 8. This construction allows also the exact positioning of e.g. sensor arrays in a geometrically well defined position.

Enlarged view of 2b shows the partially retracted guide needle 6 and the active surface of the diagnostic element 7 which is directly exposed to the subcutaneous tissue. In this example the conducting part of the diagnostic element 8 remains in the partially retracted guide needle and a flexprint is used as substrate for the active surface and conducting part of the diagnostic element. The active surface of the diagnostic element holds an electrochemical sensor 15 and the conducting part of the diagnostic element holds an insulated electric conductor line 16. It is also possible to place more than one sensor and conductor line on the same and/or opposing faces of the flexprint substrate.

FIG. 3 shows one embodiment of the means to bring the flexible base plate from the ready-to-use position to the position of the operation mode and consecutively to partially retract the guide needle. This is in the described embodiment a circular sliding bolt mechanism composed of three pieces, a plate 11 with several slits, an actuation knob 12 and a drive mechanism 21, e.g. a spring turning the plate. In this figure a mechanism for a flexible baseplate with four radial segments is shown but the principle of this mechanism can be easily adapted to more radial segments, to two segments with a diagonal slit and to a linear sliding bolt mechanism.

In the ready-to-use position the flexible base plate (not shown) is pre-stressed by pins on the segments which are restrained by the crosspieces 17 of the sliding bolt plate. Following a first rotation of e.g. 30° these pins fall into slits 18 and the baseplate thereby rapidly relaxes into a flat position. The holder of the guide needle (not shown) is pressed by a spring against the sliding bolt plate, has a cylindrical shape fitting into the central hole of the plate and has four wings which are restrained by the cross-pieces 19 of the plate in the starting position and also after the first rotation of the sliding bolt plate. Upon a second rotation of e.g. again 30° these wings fall into slits 20 and the holder of the guide needle is pressed by the spring through the central hole of the sliding bolt plate against a stop (not shown).

Consecutive actuation of the first and the second rotations of the sliding bolt plate are accomplished by releasing the drive mechanism 21 through pressing and then again releasing the actuation knob 12. The actuation knob is in a slit 22; a narrowing 23 holds the sliding bolt plate in the start position (FIG. 3a), a protruding detent 24 stops the first rotation of the sliding bolt plate (FIG. 3b) and the second rotation of the sliding bolt plate is stopped by the end of the slit 22 (FIG. 3c). The details how pressing and again releasing the actuation knob actuates these rotations consecutively are depicted in FIGS. 3A to 3C showing a cross-section of the device casing 1, of the actuation knob 12 and of the sliding bolt plate 11 with the slit 22. Further, a schematic horizontal cut at the level of the blocking interaction between actuation knob and sliding bolt plate (broken line) is shown.

FIG. 3a shows the actuation knob 12 and the sliding bolt plate 11 in the starting position. The actuation knob has a first rim 25 which is pressed by the spring 13 against the cover of the casing 1. The sliding bolt plate is under tension by the drive mechanism 21 but a second rim of the actuation knob 26 is blocking against the narrowing 23. Upon pressing the actuation knob the neck 27 between the first and the second rim is moved to and the second rim out of the plane of the narrowing and releases the first rotation of the sliding bolt plate until the detent 24 hits the $1^{st}$ rim 25 and the rotation is stopped.

FIG. 3b shows the actuation knob 12 and the sliding bolt plate 11 in the position stopped after the first rotation. In this position the pre-stressed flexible base plate has adopted a flat shape upon relaxation and the guide needle is fully inserted into the skin. Upon releasing the actuation knob it is pushed back to the starting position and the first rim 25 is moved above the plane of the detent 24 releasing the second rotation of the sliding bolt plate until the end of the slit 22 of the sliding bolt plate hits the second rim of the actuation knob 26 and the rotation is stopped.

FIG. 3c shows the actuation knob 12 and the sliding bolt plate 11 in the final position, stopped after the second rotation. In this position not only the flexible base plate has adopted a flat shape but also the guide needle is partially retracted exposing the active surface of the diagnostic element to the interstitial fluid of the skin and the control and measuring means are activated by a switch actuated at the end position of the second rotation (not shown).

Upon reading this specification, various alternative embodiments will become obvious to the skilled artisan. For example, the implantation mechanism and the partial retraction of the guide needle could be achieved via numerous chemical, mechanical, or electrical means. Further, a large variety of diagnostic elements and sensor arrays as well as control and measuring means can be accommodated with the device. In addition a micro-dialysis system may be built inserting a semi-permeable dialysis membrane into the skin with a guide needle and exposing the dialysis membrane to the subcutaneous fluid upon partial retraction of the guide needle. The dialysate solution can be pumped through the system with a micro-pump accommodated in the device and the analytes in the dialysate analysed online in the device or sampled for later analysis.

Preferred sensors for analytes fitting well with the specifications of the subject device can be constructed following state of the art procedures for electrochemical and optical sensors. The construction of miniaturized electrochemical and optical sensors is greatly improved by the use of matrix materials optimally suited for production by well established methodologies but such materials are often not suitable for direct implantation into the skin, e.g. because they are too flexible or can break if used directly to penetrate the skin. Introduction of such sensors into the skin can only be achieved with a guide needle and the described partial retraction of the guide needle greatly improves design and handling by the patient. It allows establishing permanent connections to the control and measuring means during manufacturing: connections, esp. if done following implantation by the patient are problematic with miniaturized structures or almost impossible if conduction of very low electrical or other signals or of fluid is necessary. A slit guide needle often used allowing removal after implantation leads to important tissue damage and limits miniaturization.

For the construction of electrochemical sensors silicon or flexible substrates are ideal and technologically well established but for both a guide needle is needed for implantation. The use of flexprint technologies used for PCBs in electronics is straight-forward by coating part of the active surface with a suitable sensor e.g. for glucose and manufacturing of flexprints is approaching a level of miniaturization which makes it very suitable for diagnostic elements. For the construction of optical sensors a wide variety of methods can be optimally adapted for direct determination of the analyte or for indirect monitoring using suitable indicators. Such general methods can be coupled to analyte-specific enzyme reactions or to specific binding to receptors or antibodies. The current invention provides an easy solution for establishing permanent connections to the control and measuring means during manufacturing which is very important for good performance of such miniaturized electrical or light transmitting fibres.

The invention has been described with reference to a few specific and preferred embodiments, techniques and applications. However, it will be apparent to one of ordinary skill in the art that many variations and modifications and adaptations to special applications and needs may be made while remaining within the spirit and scope of the invention.

The invention claimed is:

1. A method for exposing an active surface at a tip of a diagnostic element of a dermally affixed sensor device to a body fluid for measurement of a concentration of an analyte, comprising:
    inserting a hollow all-around closed guide needle of the dermally affixed sensor device into a patient's skin using the dermally affixed sensor device, the hollow guide needle housing the active surface and at least one connection line to control and measuring circuitry of the diagnostic element, and the at least one connection line being fixedly positioned within the dermally affixed sensor device and rigid; and
    after insertion of the hollow guide needle, retracting the hollow guide needle only partially into a casing of the dermally affixed sensor device by the hollow guide needle sliding over the at least one connection line to an extent sufficient for exposing the active surface at the tip of the diagnostic element to the body fluid, without a need to temporarily disconnect the at least one connection line between the active surface and the control and measuring circuitry of the diagnostic element.

2. The method according to claim 1, wherein the diagnostic element is a microdialysis system including a pumping system for dialysate and a semi-permeable interface or dialysis membrane as the active surface which is exposed to the body fluid.

3. The method according to claim 1, further comprising analyzing online the concentration of the analyte in a dialysate within the control and measuring circuitry.

4. The method according to claim 1, wherein the active surface includes a sensor.

5. The method according to claim 1, wherein the retracting the hollow guide needle includes sliding the hollow guide needle over the active surface and the at least one connection line that are fixedly positioned within the dermally affixed device.

6. The method according to claim 1, wherein the retracting the hollow guide needle includes at least a portion of the at least one connection line remaining housed in the hollow guide needle after the partial retraction of the hollow guide needle.

7. A dermally affixed sensor device for performing the method according to claim 1, comprising:
   the casing;
   an insertion mechanism within the dermally affixed sensor device comprising
   a flexible surface attached to the casing configured to secure adherence of the device to the patient's skin via an adhesive layer, the flexible surface including a first position in which the hollow guide needle is concealed by the flexible surface and a second position in which an implantable part of the hollow guide needle is exposed beyond the flexible surface;
   a rigid structure in the casing that holds the diagnostic element including the active surface, the active surface being connected to the at least one connection line that is between the active surface and the control and measuring circuitry;
   the hollow guide needle including an all-around around closed wall, wherein the active surface and the at least one connection line are housable in the hollow guide needle; and
   an actuator to move the flexible surface from the first to the second position, wherein
   the hollow guide needle, after being inserted, is only partially retractable into the casing by the hollow guide needle sliding over the at least one connection line to an extent sufficient for exposing the active surface at the tip of the diagnostic element to the body fluid, without a need to temporarily disconnect the at least one connection line between the active surface and the control and measuring circuitry of the diagnostic element.

8. The device according to claim 7, wherein the diagnostic element is fixedly positioned within the device.

9. The device according to claim 7, wherein the actuator includes a sliding bolt mechanism configured such that the move of the flexible surface from the first to the second position and the partial retraction of the hollow guide needle are activated consecutively by a release structure.

10. The device according to claim 9, wherein the release structure that activates the sliding bolt mechanism is a knob configured such that pressing the knob actuates the actuator which inserts the hollow guide needle into the patient's skin, and consecutively releasing the knob partially retracts the hollow guide needle.

11. The device according to claim 7, wherein the active surface is flexible or is not suited to be placed into the patient's skin without the hollow guide needle.

12. The device according to claim 7, wherein the active surface of the diagnostic element includes a diameter below 250 μm and is configured to be implanted at a depth of 1 to 5 mm in the patient's skin, and the hollow guide needle is configured to be retracted by 1 to 3 mm.

13. The device according to claim 7, wherein the active surface of the diagnostic element includes a sensor.

14. The device according to claim 7, wherein the adhesive layer is configured for temporary wearing on a body, and is fixed on the flexible surface of the device by a reduced surface in comparison to the adhesive layer that is configured to adhere to the patient's skin.

15. The device according to claim 7, wherein the device is configured to be applied to the patient's skin using a functional package protecting release elements of the device against unintended activation and including a rim that presses the adhesive layer towards the patient's skin and that secures its adhesion.

16. The device according to claim 7, further comprising the control and measuring circuitry configured to:
   a) survey correct functioning of the device,
   b) transform sensor signals into analyte measurements,
   c) store, display, and transmit the analyte measurements online or batch-wise, and
   d) give warning signals when the analyte measurements are not within a predefined range.

17. The device according to claim 7, wherein the device includes a reusable part comprising control elements and a disposable part comprising at least elements configured to adhere to the patient's skin, the hollow guide needle, the active surface and the at least one connection line.

18. The device according to claim 7, wherein the hollow guide needle is slidable over the active surface and the at least one connection line that are fixedly positioned within the device.

19. The device according to claim 7, wherein the active surface is rigidly connected to the at least one connection line that is rigidly disposed between the active surface and the control and measuring circuitry.

* * * * *